(12) United States Patent
Stamberg

(10) Patent No.: US 6,403,011 B1
(45) Date of Patent: Jun. 11, 2002

(54) METHOD OF TIP FORMING WITH MORE IMPROVED TAPERED AND LOWER TIP ENTRY PROFILE

(75) Inventor: Barbara E. Stamberg, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/465,986

(22) Filed: Dec. 16, 1999

(51) Int. Cl.[7] .............................. B26D 3/12; B26F 1/18; B29C 65/06; B29C 69/00; B32B 31/14

(52) U.S. Cl. ........................ 264/400; 156/73.5; 156/84; 156/250; 156/252; 156/272.8; 264/138; 264/163; 264/230

(58) Field of Search .................................. 264/138, 163, 264/230, 400; 156/73.5, 84, 250, 252, 272.8

(56) References Cited

U.S. PATENT DOCUMENTS

| | | | |
|---|---|---|---|
| 5,240,537 A | 8/1993 | Bodicky | 156/244.13 |
| 5,667,493 A | * 9/1997 | Janacek | 604/96 |
| 5,792,124 A | 8/1998 | Horrigan et al. | 604/282 |
| 5,811,043 A | 9/1998 | Horrigan et al. | 264/138 |
| 5,851,464 A | 12/1998 | Davila et al. | 264/103 |

* cited by examiner

Primary Examiner—Leo B. Tentoni
(74) Attorney, Agent, or Firm—Fulwider Patton Lee & Utecht, LLP

(57) ABSTRACT

The invention is directed to a method of forming a distal tip on a catheter. The method includes defining an area on the distal end of a polymeric tube, creating at least one void by removing at least some of the material within the area, and sealing the cut edge closed. The area is defined by a boundary, which includes a first location on the distal tip, a second location on the distal tip radially spaced apart from the first location, and a third location proximal to the distal tip. The preferred area is a cut having a V-shape. This method creates a superior catheter tip profile, specifically for soft tips.

16 Claims, 2 Drawing Sheets

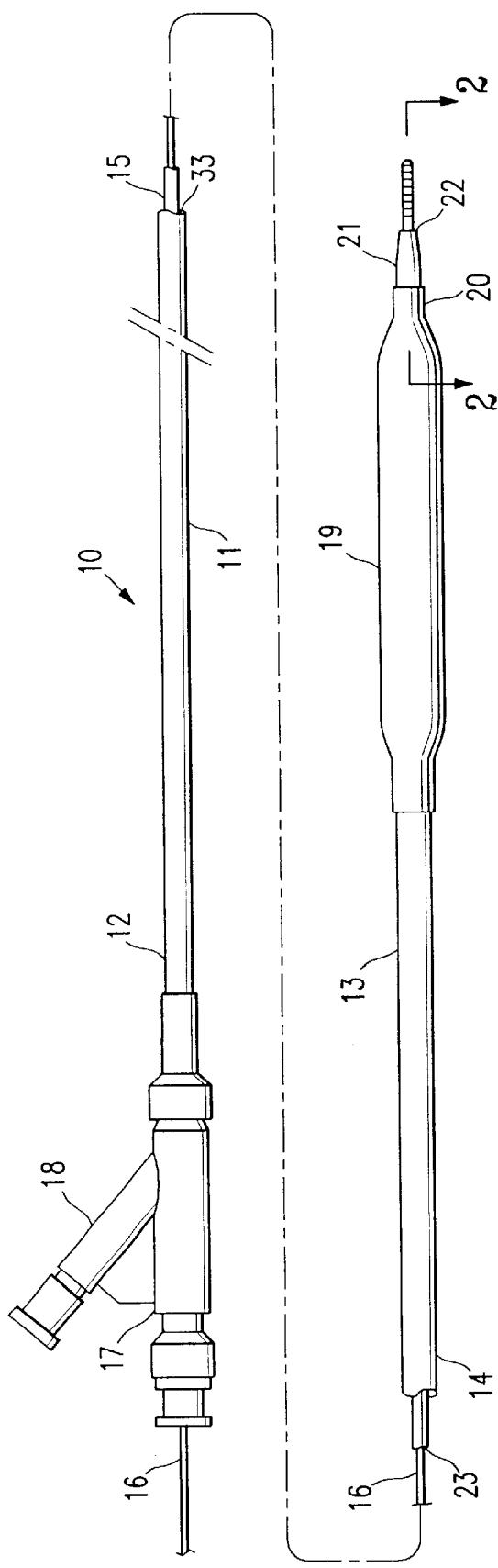
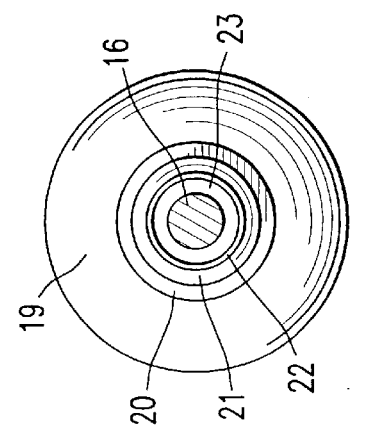
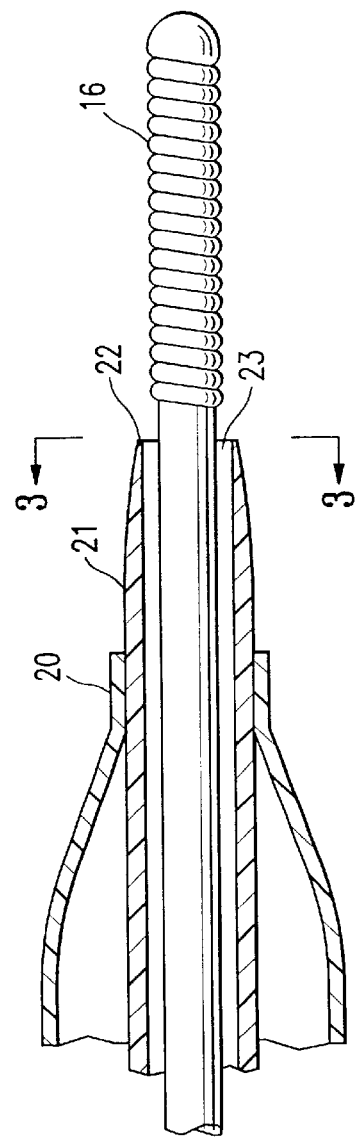
FIG. 1
FIG. 2
FIG. 3

METHOD OF TIP FORMING WITH MORE IMPROVED TAPERED AND LOWER TIP ENTRY PROFILE

BACKGROUND OF THE INVENTION

This invention generally relates to the field of intracorporeal catheters, and more particularly to a method of forming a distal tip on a catheter with a uniform taper and a low tip entry profile.

Percutaneous transluminal coronary angioplasty (PTCA) is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery and the distal tip of the guiding catheter is then maneuvered into the ostium.

Catheters must have sufficient stiffness to be pushed through vessels as well as sufficient rigidity to provide a high degree of torsional control. However, stiffness or rigidity in the catheter tip poses the danger of puncturing or otherwise damaging a vessel lining as the catheter advances through the vascular system. It is therefore desirable for catheters to have a soft or flexible distal tip.

These types of catheters must also have an extremely small outside diameter because they are used in an intravascular environment. This is especially true of the distal tip, which has the first contact with the inner walls of the vascular system. A small outer diameter on the distal tip creates a smaller entry profile.

Therefore, what has been needed is a method to form the tips of a catheter that will improve the entry profile and have a smaller outside diameter. The present invention satisfies these and other needs.

SUMMARY OF THE INVENTION

The invention is directed to a method of forming a distal tip on a catheter. The method comprises defining an area on the distal end of a polymeric tube, creating at least one void by removing at least some of the material within the area, and sealing the void closed. The distal end has a distal tip. The area has a first location on the distal tip, a second location on the distal tip radially spaced apart from the first location, a third location proximal to the first and second locations, and a boundary including the first location, the second location and the third location. One embodiment of the invention has one area defined, while other embodiments have two or more areas defined for material removal at points about the distal tip.

In one embodiment of the invention, the polymeric tube is a catheter shaft. Specifically, a catheter distal end. The catheter distal end may be an extension of the inner member of the catheter, or an attachment that is a softer material than the majority of the material making up the catheter shaft. In some embodiments, the polymeric tube is a layered tube, with two, three, or more layers of material forming the polymeric tube. In layered embodiments, the layers preferably have compatible melting temperatures to achieve uniform and comparable taper in each layer.

In a presently preferred method, a polymeric tube is placed on a mandrel having an outer diameter equal to the desired inner diameter of the distal end. The polymeric tube will have a proximal end, a distal end with a distal tip and an inner and outer surface. The preferred embodiment of the invention then provides a cutting apparatus. Any of several cutting techniques known in the art, including but not limited to a laser, a cutting blade and a hot wire are suitable for the present method. The cutting apparatus will perform a cut on the distal end of the polymer tube. The cut will have a first location on the distal tip, a second location on the distal tip and a third location proximal to the first and second locations. The third location will be preferably spaced along the radial face between the first location and the second location. The distal end then has a cut edge that includes the first location, the second location and the third location. The cut edge may take any shape, including a U shape or a stepped shape. In a specific embodiment, the cut edge is a V shape.

Additional embodiments of the invention include removing one or multiple volumes of material from the defined area. By way of example and not as a limitation, this could be accomplished by subjecting the distal end to a laser beam. The one or multiple volumes may have any shape. Additionally, the volumes need not touch, which would leave residue material within the area.

The first location is about 0.004 inches (0.102 mm) to about 0.008 inches (0.203 mm) from the second location. In one specific embodiment, the polymeric tube is a catheter for a 0.014 inch (0.356 mm) guidewire system. The catheter has an inner diameter of 0.016 inch (0.406 mm), and an outer diameter of about 0.023 inch (0.584 mm) to about 0.025 inch (0.635 mm). For this catheter, the first location is about 0.005 inches (0.147 mm) to about 0.007 inches (0.177 mm) from the second location.

The third location is proximal to the first and second locations. The third location is typically about 0.01 inches (0.254 mm) to about 0.02 inches (0.508 mm) from the distal tip along the longitudinal axis. For the 0.014 inch (0.356 mm) guidewire system described above, the third location was about 0.013 inches (0.3302 mm) to about 0.017 inches (0.432 mm) from the distal tip.

After the area has been defined, at least a portion of the material within the area is removed from the polymeric tube. This results in a void of material on the distal end, specifically a V-shaped recess. For the 0.014 inch system described above, the removed material resulted in a V-shape area, with an angle at the proximal location of about 10 degrees to about 44 degrees.

In the V-shape cut embodiment, removing the material also results in the creation of a face between the inner surface of the polymeric tube and the outer surface at the first location and a similar face at the second location. For the purpose of this patent, this face is defined as a radial face. In certain embodiments, the radial face at the first location may have an angle of about 5 degrees to about 30 degrees with respect to the radial face at the second location. Specifically, the angle is about 10 degrees to about 20 degrees.

The tube is then sealed using a suitable method such as heat sealing. Additional sealing processes include, but are not limited to, adhesive, fusion or laser welding and heat shrinking. Laser welding and heat shrinking are preferred sealing processes.

The method of forming a distal tip of this invention provides for a distal end with a uniform taper to the distal tip. Additionally, the distal tip has a low entry profile, easing entry into the vasculature. These and other advantages of the invention will become more apparent from the following detailed description of the invention and the accompanying exemplary drawings.

BRIEF DESCRIPTION OF THE DRAWINGS

FIG. 1 is an elevational view of a balloon catheter that embodies features of the invention, showing the balloon in an expanded state and the distal tip as an extension of the catheter inner member.

FIG. 2 is a longitudinal cross. sectional view of the catheter system of FIG. 1 taken along line 2—2.

FIG. 3 is a transverse cross sectional view of the catheter system of FIG. 2 taken along line 3—3.

DETAILED DESCRIPTION OF THE INVENTION

Figure 5:
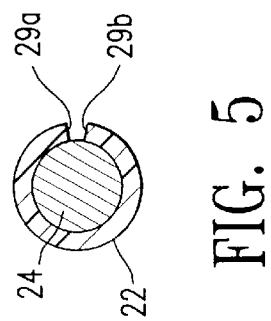
FIG. 5 is a transverse cross sectional view of the catheter system of FIG. 4 taken along line 5—5.

FIGS. 1–3 illustrate a balloon catheter 10 embodying features of the invention which generally include an elongated catheter shaft 11 having a proximal section 12 and a distal section 13 and a balloon 19 mounted on the distal shaft section 13. In the embodiment shown in FIG. 1, an adapter 17 is mounted on the proximal shaft section 12. A guidewire 16 is disposed within the guidewire lumen 23 defined by the inner tubular member 15. Outer tubular member 14, together with inner tubular member 15, defines an inflation lumen 33 in fluid communication with balloon 19 and an inflation port 18 on an adapter 17. Inflation fluid may be introduced into the inflation port 18, through the inflation lumen 33, and subsequently inflate the balloon 19.

In the embodiment shown in FIG. 1, the balloon 19 is sealingly secured to the inner member 15. The balloon 19 has a distal end 20 secured to the catheter shaft 11. The catheter 10 has a distal end 21 distal to the balloon distal end 20. In the embodiment shown in FIG. 1, the distal end 21 is shown as an extension of inner member 15. In alternative embodiments, the distal end 21 could be a separate element joined to the inner member 15, and formed of a substantially softer material than the catheter shaft 11. The distal end 21 tapers to the distal tip 22. At the distal tip 22, the outer diameter has reduced to create a small entry profile.

FIGS. 4 through 7 illustrate in a generally sequential manner, the more important steps of a preferred embodiment of the present invention. This embodiment illustrates the V-shape cut out embodiment. The method described here can be used to manufacture a variety of tips, such as the tip 22 shown in FIG. 1. In addition, this method could be used to manufacture tips on a catheter without a balloon, or on one that would be used in body lumens other than the arteries. This method could also be used to form a taper on a polymer tube to facilitate a joint with another polymer tube that would fit over the tapered portion. This method could be used to create a tapered tip for a variety of medical devices where a tapered tip would be advantageous.

Figure 4:
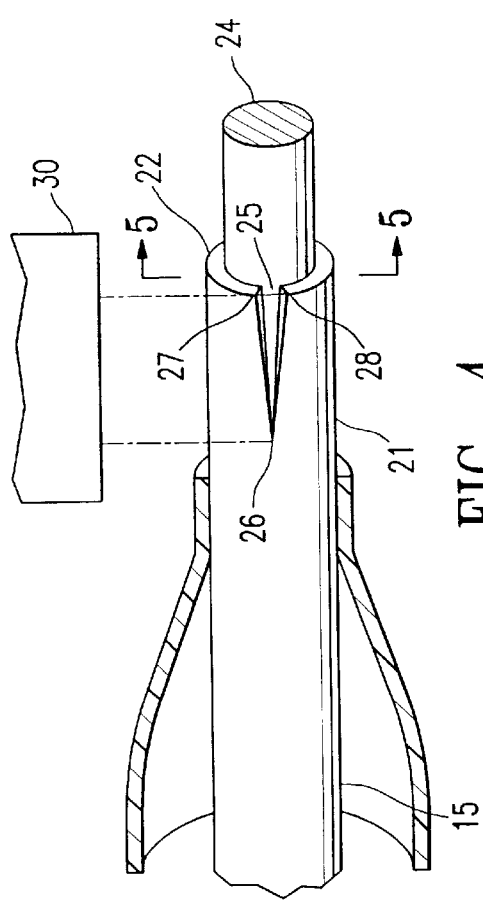
FIG. 4 is a perspective view, partially in section, of the distal end of the catheter system of FIG. 1 during the cutting and removing phase of the present invention.

FIG. 4 illustrates a cutting machine 30 performing a cut out 25 on the distal end 21. The distal end 21 is placed on a mandrel 24. The cutting machine 30 performs the cut out 25 by entering the distal tip 22 at a first location 27 and a second location 28. The two locations lead to a third location 26, which is proximal to the distal tip 22. The cut out 25 defines a volume of material, which is then removed from the distal end 21. Removing the material creates two radial surfaces 29 on the distal tip 22. One radial surface 29a at the first location 27 and a second radial face 29b at the second location 28. FIG. 5 is a transverse cross sectional view of the distal end of the tip system shown in FIG. 4 along the line 5—5.

Figure 6:
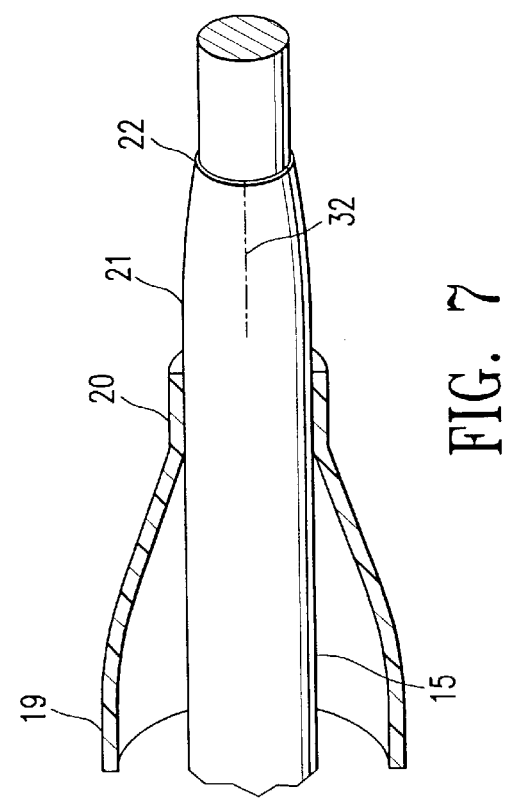
FIG. 6 is a perspective view, partially in section, of the distal end of the catheter system of FIG. 1 during the sealing phase of the present invention.
Figure 7:
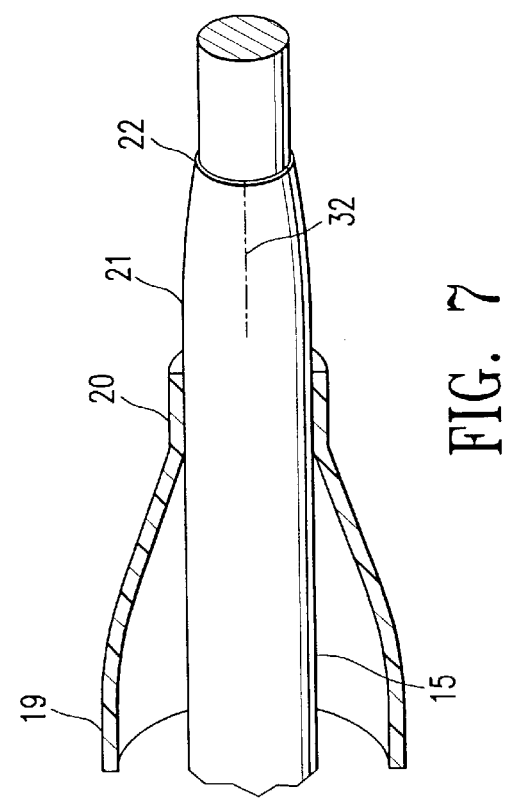
FIG. 7 is a perspective view of the completed distal end of the catheter system of FIG. 1, partially in section.

FIG. 6 illustrates the application of heat through a heat-sealing source 31. The application of a sealing process, like a heat source 31, causes the polymer to flow and to seal the cut 25. FIG. 7 illustrates the distal end 21 of the catheter system after the sealing process is complete. The seal 32 is illustrated in phantom, as the seal is invisible on the actual apparatus. The distal tip 22 has a greater percentage of its material removed than locations on the distal end 21 proximal to the distal tip 22. Therefore, when the polymer flows, the distal tip 22 material must thin to close the gap created by the cut 25. As a result, the distal tip 22 has a low entry profile, and the distal end 21 tapers toward the distal tip 22 from a larger transverse dimension to a smaller transverse dimension.

Although individual features of embodiments of the invention may be shown in some of the drawings and not in others, those skilled in the art will recognize that individual features of one embodiment of the invention can be combined with any or all the features of another embodiment.

What is claimed is:

1. A method for forming a tapered catheter tip comprising
    a) defining an area on a distal end of a tubular catheter member which is made of polymeric material and which has a distal tip;
    b) the area having a first location on the distal tip, a second location on the distal tip radially spaced apart from the first location, a third location proximal to the distal tip, and a boundary including the first location, the second location and the third location;
    c) creating at least one void by removing at least some material from within the area; and
    d) sealing the void closed to form the tapered catheter tip.

2. The method of claim 1 wherein the boundary is a cut edge, and all the material within the area is removed.

3. The method of claim 1 wherein the polymeric tube is a catheter shaft.

4. The method of claim 1 wherein the polymeric tube is a catheter soft tip.

5. The method of claim 1 wherein the polymeric tube has at least two layers.

6. The method of claim 1 wherein the polymeric tube has at least three layers.

7. The method of claim 1 wherein the third location is radially spaced between the first and second locations.

8. The method of claim 1 wherein at least two areas are defined.

9. The method of claim 1 wherein the first location is about 0.004 inches (0.102 mm) to about 0.008 inches (0.203 mm) from the second location.

10. The method of claim 1 wherein the first location is about 0.0055 inches (0.147 mm) to about 0.0065 inches (0.165 mm) from the second location.

11. The method of claim 1 wherein the third location is about 0.01 inches (0.254 mm) to about 0.02 inches (0.508 mm) from the distal end.

12. The method of claim 1 wherein the third location is about 0.013 inches (0.33 mm) to about 0.018 inches (0.432 mm) from the distal end.

13. The method of claim 2 wherein the cut edge forms a V shape.

14. The method of claim 2 wherein the cut edge forms a V-shape having an angle at the third location of about 10 degrees to about 44 degrees.

15. The method of claim 2 further comprising a radial face at the first location, a radial face at the second location, the first radial face having an angle of about 5 degrees to about 30 degrees with respect to the second radial face.

16. The method of claim 2 further comprising a radial face at the first location, a radial face at the second location, the first radial face having an angle of about 10 degrees to about 20 degrees with respect to the second radial face.

* * * * *